United States Patent [19]
Pentoney, Jr.

[11] Patent Number: 5,208,466
[45] Date of Patent: May 4, 1993

[54] APPARATUS AND METHOD FOR ALIGNING CAPILLARY COLUMN AND DETECTION OPTICS

[75] Inventor: Stephen L. Pentoney, Jr., Yorba Linda, Calif.

[73] Assignee: Beckman Instruments, Inc., Fullerton, Calif.

[21] Appl. No.: 772,997

[22] Filed: Oct. 8, 1991

[51] Int. Cl.$^5$ .............................................. G01N 27/00
[52] U.S. Cl. .................... 250/574; 204/299 R
[58] Field of Search ............. 250/206.1, 206.2, 227.29, 250/574, 575, 576; 356/244, 339, 344; 204/180.1, 182.8, 183.3, 299 R; 436/172

[56] References Cited
U.S. PATENT DOCUMENTS

| | | | |
|---|---|---|---|
| 4,154,669 | 5/1979 | Goetz | 204/299 R |
| 4,239,612 | 12/1980 | Goetz | 204/299 R |
| 4,675,300 | 6/1987 | Zare et al. | 436/172 |
| 5,100,529 | 3/1992 | Fujii | 356/344 |

Primary Examiner—David C. Nelms
Assistant Examiner—John R. Lee
Attorney, Agent, or Firm—William H. May; Paul R. Harder; Wen Liu

[57] ABSTRACT

An apparatus xxx method of aligning a capillary with respect to a radiation source. More particularly, the capillary is aligned with a laser beam for laser induced fluorescence detection. The light reflection/scatter pattern of the laser beam originating from the capillary wall is utilized to determine optimum alignment. Photosensors may be implemented to detect the scatter pattern which represents optimum alignment. For dynamic alignment during electrophoresis, the photosensors provide feedback to a controller which controls a positioning mechanism for alignment of the capillary.

24 Claims, 5 Drawing Sheets

APPARATUS AND METHOD FOR ALIGNING CAPILLARY COLUMN AND DETECTION OPTICS

BACKGROUND OF THE INVENTION

1. Field of the Invention

The present invention relates to optical detection of macromolecular components separated in a capillary column, and more particularly to the alignment of the capillary column with the detection optics.

2. Description of Related Art

Macromolecules of a biological sample can be separated in a capillary column by means of several techniques. One of the techniques is capillary electrophoresis in which a sample is separated in a capillary channel by application of a high electric potential along the capillary channel. The sample separates into zones of macromolecule species as a result of different mobilities within the separation medium that are inherent to the macromolecules, depending on their electric charges, sizes, and shapes.

The separated zones can be detected by several techniques. One of many optical detection techniques is laser induced fluorescence detection. Reference is made to U.S. Pat. No. 4,675,300 to Zare et al for a detailed description of the detection technique. In general light from a laser source is passed through a section of a capillary separation channel to cause the separated sample components which were tagged with fluorescent material prior to, during or just after separation to fluoresce. The fluorescence may be detected with high sensitivity. High sensitivity and maximum resolution are achieved by concentrating the laser beam into a narrow spot which interrogates a short section of the capillary separation channel defining a small detection volume. A typical size for the spot is on the order of 50 microns or less for a separation channel having a diameter of the same order or larger.

Like any other optical detection scheme, maximum sensitivity is achieved for laser induced fluorescence detection only when the entire configuration of the laser beam, capillary separation channel and optical elements are properly aligned. A critical component of proper optical alignment is the positioning of the capillary detection volume with respect to the laser beam. Because typical detection volumes and capillary dimensions are extremely small, misalignment of the capillary channel and the laser beam by only a few microns may seriously degrade detector performance.

It is difficult to correctly position the capillary in the laser beam to achieve perfect alignment, and to maintain this position once it is achieved. Factors compounding this difficulty include the requirement that capillaries be readily replaceable and the fact that the capillary may flex under application of high electric fields. The exact cause of the capillary motion is uncertain. One suspects that the charge distribution in the capillary channel accompanied by time-dependent changes in the electric field at the inside walls of the capillary column may be part of the cause.

One current approach to aligning an open-tube capillary (filled with electrolyte solution as opposed to packed capillary which are filled with gel electrolyte or the like materials) prior to an electrophoresis run is to pump into the capillary a fluorescent solution and adjust the alignment while monitoring the fluorescence with either a photomultiplier tube or a photodiode. Alignment is considered achieved when the fluorescence intensity is at a maximum.

The above-described means of alignment is applicable only to open tube capillaries, i.e. filled only with liquid electrolyte, not gel, since fluorescent solution cannot be effectively pumped into a gel-filled column before alignment and later completely removed from the gel after alignment. This means also is undesirable in an open tube because it is often difficult or impossible to completely remove the fluorescent material from the capillary inner walls afterwards. Furthermore, there is no provision for performing dynamic alignment during an electrophoretic process. Since the capillary column tends to flex laterally under the high applied electric potential to result in misalignment of the separation channel with respect to the laser beam, there is no way of knowing when the alignment has drifted away from optimum during an electrophoresis operation.

SUMMARY OF THE INVENTION

The present invention is directed to an apparatus and method for aligning a capillary channel with respect to a radiation source. The method relies on the distinctive and reproducible radiation scatter pattern produced at the interface between the capillary channel wall and the capillary content. The method also relies on the distinctive and reproducible transmitted beam pattern observed after passage through the capillary. The method does not require the presence of fluorescent material and is applicable to open-tube and gel-filled capillaries. The alignment procedure can be performed at any stage of a process, e.g. electrophoresis, that requires proper alignment of a capillary channel with respect to a radiation source.

Radiation from a source, e.g. a laser beam, is focused on the capillary separation channel. Looking through a microscope objective, the capillary is moved laterally with respect to the radiation source until a distinct scatter pattern is observed originating from the interface between the capillary inside wall and the capillary content in a diametral plane in a perpendicular direction to the laser beam. Alternatively, alignment is determined from the far field image of the scatter pattern. Photosensors may be employed to detect the scatter pattern. The output of the photosensors may be applied to control a servo mechanism which adjusts the lateral position of the capillary separation channel with respect to the laser beam to obtain the scatter pattern corresponding to optimum optical alignment. In other words, the photosensors provides feedback on the alignment condition to accomplish dynamic alignment whereby the alignment is checked and continuously corrected during electrophoresis operation.

DESCRIPTION OF THE ILLUSTRATED EMBODIMENT

The following description is of the best presently contemplated mode of carrying out the invention. This description is made for the purpose of illustrating the general principles of the invention and should not be taken in a limiting sense. The scope of the invention is best determined by reference to the appended claims.

While the present invention is described hereinbelow in reference to capillary electrophoresis, it is however understood that the present invention is not limited to such application but is applicable to alignment of a capillary channel and a radiation source in other context as well.

Figure 1:
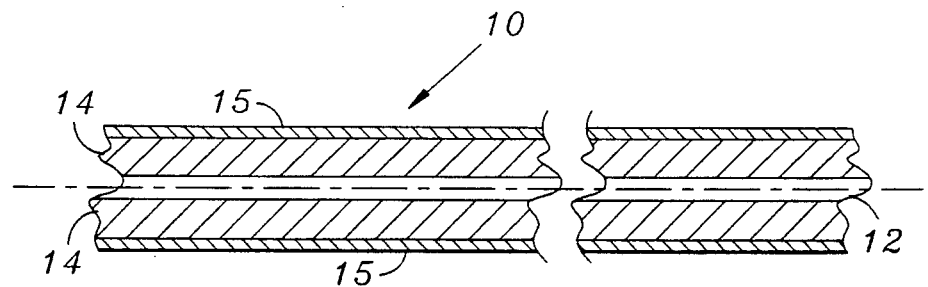
FIG. 1 is a diametral sectional view of a capillary tube.

A capillary tube 10 is shown in diametral sectional view in FIG. 1. The tube defines a cylindrical separation channel 12 of capillary dimension on the order of 5-500 micron, typically less than 200 micron. The cylindrical wall 14 of the capillary tube 10 can be made of glass, fused silica, or organic material such as teflon. To strengthen the wall 14, a polyimide coating 15 is bonded to its external surface. The capillary tube 10 is generally flexible, i.e. can be bent onto smooth curves.

Figure 2:
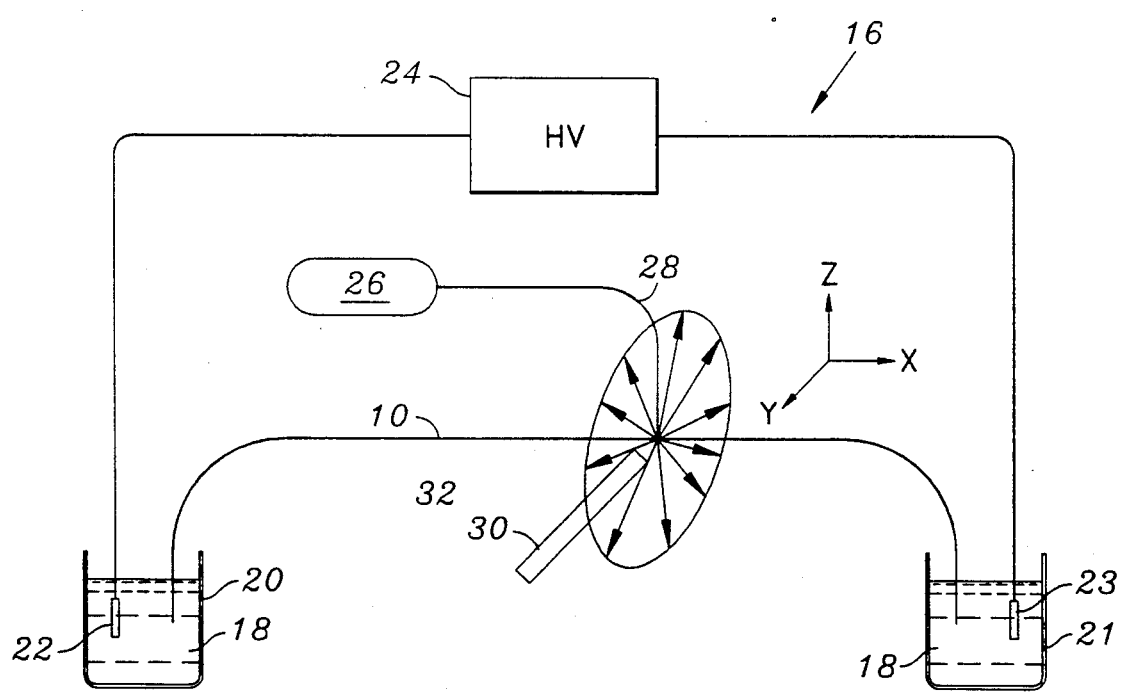
FIG. 2 is a schematic of a capillary electrophoresis apparatus with laser induced fluorescence detection.

FIG. 2 illustrates a schematic arrangement of a capillary electrophoresis apparatus 16, and more particularly one in which detection is accomplished by laser induced fluorescence. The two ends of the capillary tube 10 are submerged in electrolyte 18 contained in reservoirs 20 and 21. A high voltage power supply 24 capable of applying a high electric field (typically 1-30 KV) is electrically connected to the electrolyte 18 in the reservoirs 20 and 21 using electrodes 22 and 23. The separation channel is filled with a separation support medium which may be a electrolyte solution, gel electrolyte or other suitable conductive media. Prior to electrophoresis, a sample to be electrophoretically separated is injected into one end of the separation channel 12. This can be done by any number of conventional techniques. With the two ends of the capillary tube 10 dipped into the electrolyte 18, the high voltage power supply 24 is turned on to cause electrophoresis of the sample which results in separation into its components.

In order to be able to detect fluorescence of the separated components of the sample, it is tagged with a fluorescent material such as fluorescein. For laser induced fluorescence detection, a laser 26 is used as the excitation source. The laser 26 can be, for example, an air cooled argon ion, helium-neon laser or helium-cadmium laser having an output in the range of 100 milliwatts. A 50 micron optic fiber 28 can be used to direct the laser output to a detection section along the capillary tube 10, or a lens may focus the beam directly into the capillary (not shown). At this section, the polyimide protective coating 15 has been removed to allow the laser light to penetrate the capillary wall 14 to the separation channel 12 (see FIG. 3). Instead of using a laser source, other radiation sources can be used to excite fluorescence of the fluorescent tags in the sample components.

The laser beam is directed at 90° to the axis of the capillary tube 10. When the sample components pass by the laser beam, they are caused to fluoresce and a photomultiplier tube 30 may be positioned orthogonal to the capillary tube 10 as well as the optic fiber 28 to detect the fluorescence. The time of detected fluorescence indicates the relative migration rates of the separated components which allows identification of the components. Also, by selecting different fluorescent tags for the sample, separated components can be identified.

Figure 3:
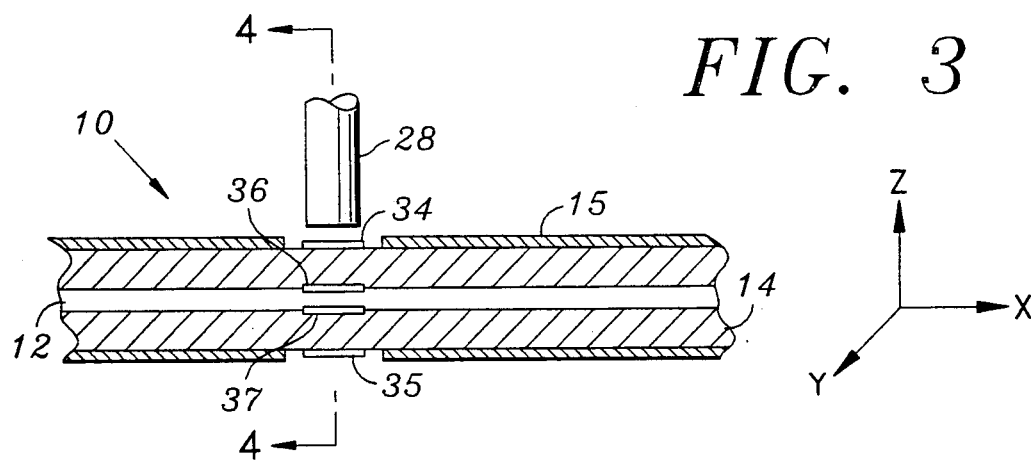
FIG. 3 is a diametral sectional view of the detection section of the capillary tube.

Besides fluorescence, the laser beam causes light scattering at the capillary tube. The term "scatter" as used herein also includes light reflection, diffraction, and other mechanisms by which light deviates from its incident direction as it comes across a change in material or refractive index in its path. Specifically, the internal and external interfaces at the capillary walls cause scattering 32 of the laser beam in all directions in a plane perpendicular to the capillary tube. Referring to FIG. 3, the diametral section of the detection section of the capillary tube 10 is shown in detail. Because of changes in refractive index at the interfaces 34 and 35 between the outer capillary surfaces and air, and the interfaces 36 and 37 between the inner capillary surface and the contents in the capillary channel 12, the laser beam is caused to scatter at these interfaces. One can readily realize that light will scatter from the four locations 34 to 37 identified in FIG. 3 when the laser beam is aligned with the diameter of the capillary tube 10, i.e. in the diametral plane. This becomes one basic premise of the present invention.

Researchers in the past have intentionally avoided the effect of light scatter in fluorescence detection. No one has advantageously made use of the distinctive and reproducible scatter originating from the capillary walls as shown in FIG. 3. The present invention makes use of this distinctive and reproducible scatter pattern to indicate optimum alignment of the radiation beam and the separation channel. To aid in further description of the invention, a coordinate system is defined in FIG. 3. The axis of the capillary tube is along the x-axis, the laser beam is along the z-axis perpendicular to the capillary tube, and the y-axis is perpendicular to both the x and z axes.

Figure 4:
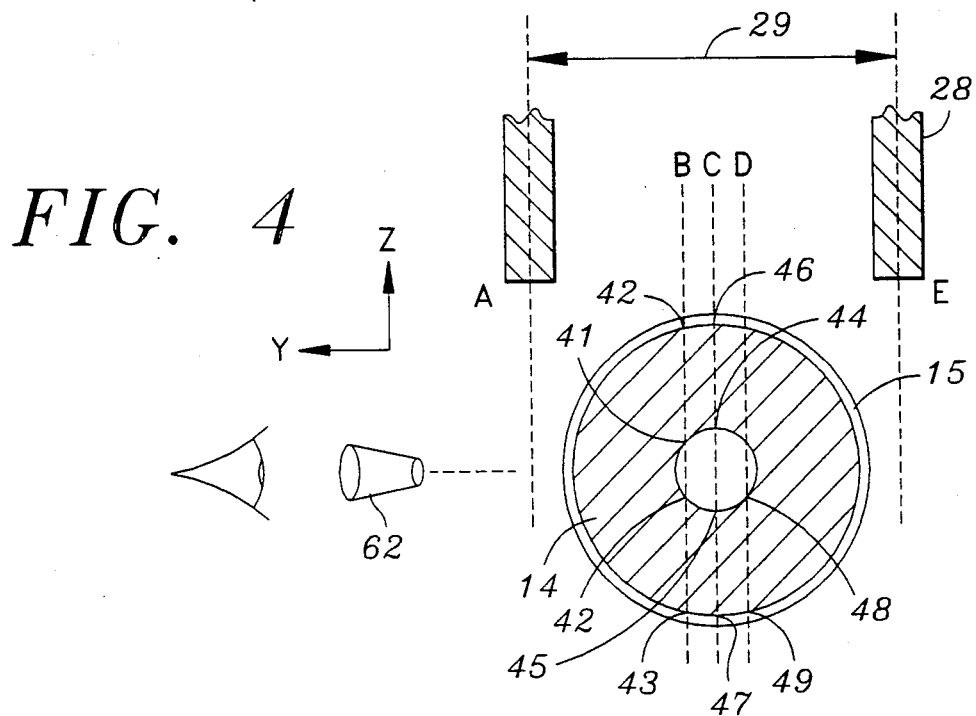
FIG. 4 is a sectional drawing indicating the various positions of the laser beam optic fiber with respect to the capillary separation channel.
Figure 5:
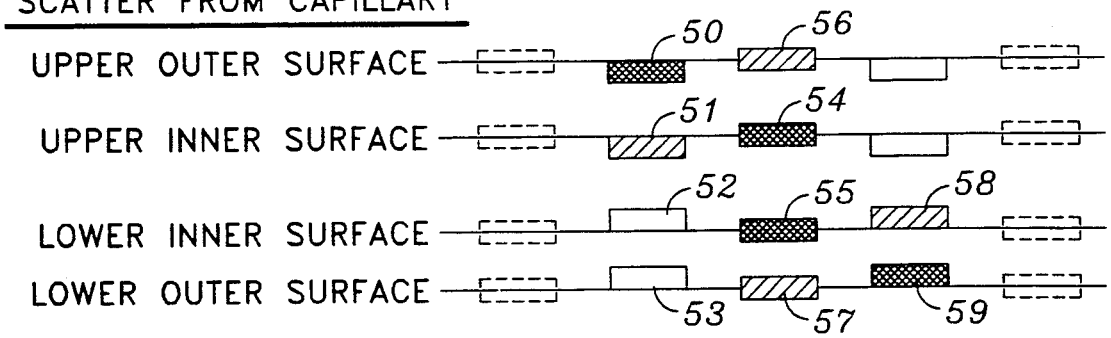
FIG. 5 represents the scatter patterns observed under a microscope objective for the various positions in FIG. 4.

Using a microscope objective 62 (FIG. 4) along the Y-axis focused on the diametral plane, the scatter patterns observed in the Y-axis at various stages of alignment are represented in FIG. 5, i.e. the scatter patterns produced when the laser beam is positioned at various locations A-E with respect to the capillary tube along the arrow 29 in the y-axis. Positions A-E are indicated in the sectional drawing in FIG. 4. Each scatter band shown in FIG. 5 originates from the interface between the capillary surface (inner or outer) and the adjacent medium (air or separation support medium). At position A, the laser beam does not hit the capillary tube 10. At position B, the laser beam hits the capillary tube 10 but is not aligned with the center of the capillary tube 10. A bright band 50 of light is observed at the left (FIG. 4) top outer surface 40 of the capillary tube 10 and a less bright band 51 is observed at the left upper inner surface 41 of the capillary wall 14. Because of the angles between the lower inner and outer surfaces 42 and 43 of the capillary wall with respect to the laser beam, the scatter bands 52 and 53 at these surfaces are less noticeable.

At position C, the laser beam is aligned with the center of the capillary tube (the diametral plane), i.e. the optimum alignment position for laser induced fluorescence. In this position, two sharp and bright bands 54 and 55 are observed at the upper and lower inner surfaces 44 and 45 of the capillary walls. Two other bright bands 56 and 57 are observed at the outer surfaces 46 and 47 of the capillary walls. Since the microscope objective is focused on the diametral plane of the capillary tube, the bands 54 and 55 appear to be brighter and sharper than the bands observed when the capillary tube is not at optimum alignment.

At position D, scatter bands 58 and 59 are observed at the lower inner and outer surfaces 48 and 49 of the capillary wall in a reverse pattern as that observed at position B. At position E, the laser beam is again out of range of the capillary tube 10 as at position A.

Figure 8:
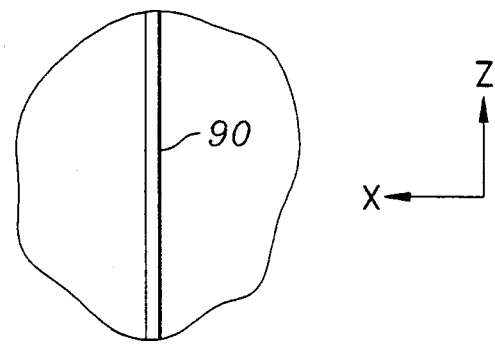
FIG. 8 represents the image of the scatter observed at far field without using a microscope objective.

It is noted that the scatter patterns shown in FIGS. 3 and 5 are the images observed under an objective lens focused at the diametral section of the capillary tube. It is understood that when the scattered light is viewed at far field without an objective lens the image of the scatter appears as a strip 90 perpendicular to the capillary tube (FIG. 8).

Figure 6:
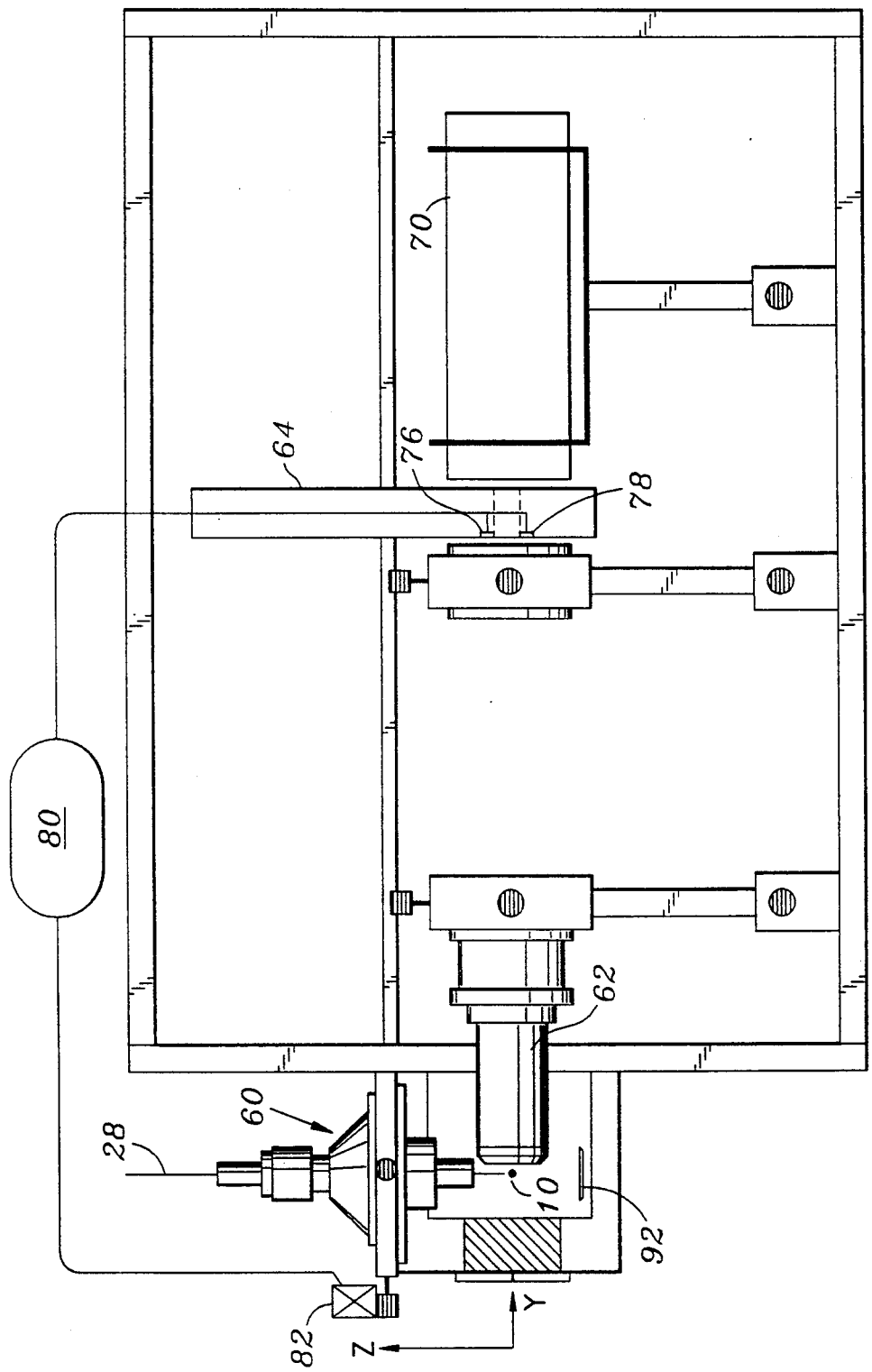
FIG. 6 is a schematic drawing of the dynamic alignment apparatus of the present invention.
Figure 7:
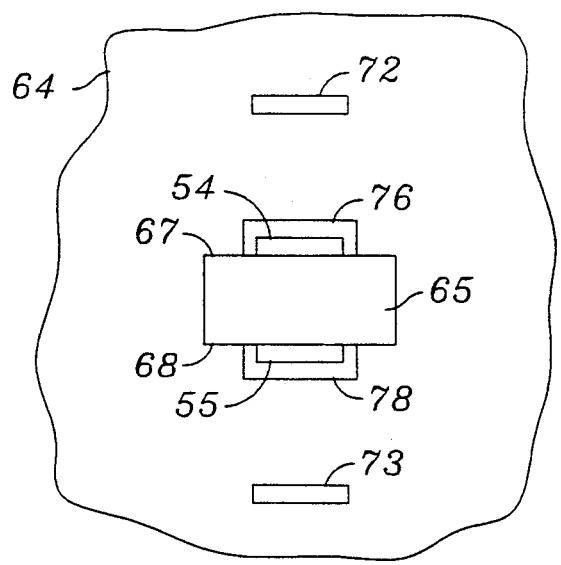
FIG. 7 is a diagram showing the image plane at the aperture plate.

Referring to FIG. 6, one embodiment of the apparatus for alignment is schematically illustrated. The optic fiber 28 which transmits the laser beam is supported by a micropositioning mechanism 60 which allows adjustment of the optic fiber 28 along the x and y axis. A microscope objective lens 62 focuses on the diametral plane of the detection section of the capillary tube 10 which is illuminated by the laser beam through the optic fiber 28. (The capillary tube 10 is perpendicular to the plane of the drawing in the x-axis.) The image of the detection section is focused onto an imaging plane defined by a plate 64. The plate 64 has an aperture 65 as shown in FIG. 7. The image of the scatter bands 54 and 55 originating from the upper and lower inner surfaces of the capillary wall are focused on the upper and lower edges 67 and 68 of the aperture 65. The aperture 65 allows the passage of most of the fluorescence from the capillary separation channel to pass onto a photomultiplier tube 70 while blocking off the scatter bands 54 and 55 as well as any scatter bands 56 and 57 originating from the outer capillary surfaces. The alignment of the optic fiber 28 with respect to the capillary tube 10 is optimum when the scatter bands 54 and 55 appear to be sharp and of nearly equal intensity (or of a particular intensity ratio depending on calibration) at the edges of the rectangular aperture. Accordingly, the source scatter which is generally regarded as an unwanted source of background signal in laser induced fluorescence is applied to optimize optical alignment. The alignment method described above simply uses the well defined radiation scatter pattern to optimize optimal alignment while simultaneously eliminating the scatter from the fluorescence signal.

It was observed that the alignment may change significantly as electric field is applied to subject the sample to electrophoresis. This is perhaps due to the electrical tension within the capillary tube 10 causing the capillary tube to flex, or the static electrical interaction between the capillary tube and the optic fiber 28. There is therefore a need to dynamically realign the optic fiber 28 and the capillary tube 10 during electrophoresis. Dynamic realignment can be made possible by placing a photosensor 76, 78 near each edge 67, 68 of the rectangular aperture 65 where the scatter bands are expected to be focused at optimum alignment. The signals from the photosensors 76 and 78 are input to a controller 80 which controls the movement of a servo or stepper motor 82 which translates the optic fiber 28 in the y-direction. The controller causes the motor to search for the optimum alignment position which is achieved when both photosensors 76 and 78 detect scatter bands 54 and 55 and that both bands are detected to be of the same intensity (or a particular intensity ratio depending on calibration). The circuit and logic of the controller 80 are apparent to one skilled in the art given the desired alignment function to be accomplished, and therefore will not be elaborated here. It is understood that provision has to be made to calibrate or balance the responses of the two photosensors due to manufacturing tolerance.

It has been found that the most critical alignment of the optics for detection purposes is between the laser beam, i.e. optic fiber 28, and the capillary tube 10. The focusing of the capillary tube 10 with respect to the microscope objective 62 is not as critical as the alignment between the laser beam and the capillary tube 10. The fluorescence detection system is relatively less sensitive to focusing of the capillary tube 10 with respect to the microscope objective 62 than the alignment of the capillary tube 10 with respect to the laser beam.

The signals from the two photosensors 76 and 78 provide feedback to automatically adjust the alignment of the capillary tube 10 and the optic fiber 28. It is possible to add additional photosensors along the edge of the aperture to provide feedback to automatically adjust the focusing of the microscope objective.

The photosensors and aperture combination serves a dual role here. The aperture plate acts as a spatial filter, physically blocking substantially the scatter bands in passing the fluorescence from the capillary contents to the photomultiplier tube 70. The photosensors provided on the aperture plate provide a means of feedback used to automatically align the laser beam and the capillary separation channel. It is noted that with the present method, it is not necessary to have fluorescent sample present in the detection volume during alignment. In fact, alignment may be maintained continuously during electrophoresis. Because alignment is based upon proper imaging of the source scatter pattern, rather than sample fluorescence, it is possible to optimize the alignment of gel or other stabilizer filled capillaries.

Figure 9:
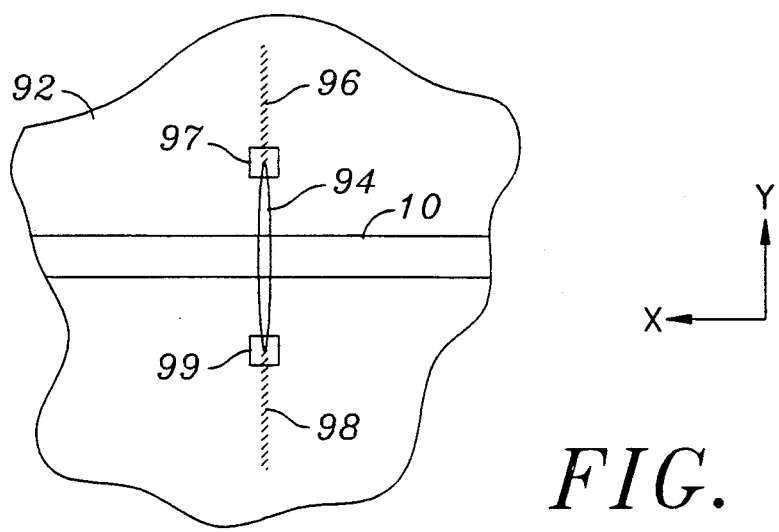
FIG. 9 represents the scatter pattern observed diametrally across the capillary tube.

Another method of alignment relies on a scatter pattern observed diametrically across the capillary tube 10 from the incident laser beam. Referring to FIG. 6, an imaging plane 92 positioned perpendicular to the direction of the laser beam and parallel to the capillary tube 10 will image a pattern of the transmitted laser light after passage through the capillary as well as scattered light. FIG. 9 represents the pattern observed when there is alignment of the capillary tube with a laser beam which is focused at the capillary tube. For gel-filled capillaries (the image differs slightly for open tube mode of operation but is very similar), there is a bright elongated spot 94 symmetrical and centered about the axis of the laser beam. This spot 94 is produced by the "lens" action of the capillary and the separation support medium therein, which function essentially as a cylindrical lens, on the transmitted laser beam. On both sides of the bright spot 94 are the symmetrical images 96 and 98 of light scattered from the capillary walls, which in this case are not as bright and sharp as the spot 94 because of the imaging position diametrally across the capillary tube from the laser beam. It has been observed that when the capillary tube is out of alignment, the resultant image will deviate from the symmetrical image shown in FIG. 9 in a manner analogous to that described above for the scatter pattern discussed with referenced to FIG. 5. Therefore the position of the transitions from the bright spot 94 to the scattered light image 96 and 98 is relied upon for alignment and accordingly appropriate photosensors 97 and 99 can be positioned on the image plane 92 to detect such transitions to confirm alignment. The outputs from the photosensors 97 and 99 can be used as feedback for automatic alignment.

Figure 10:
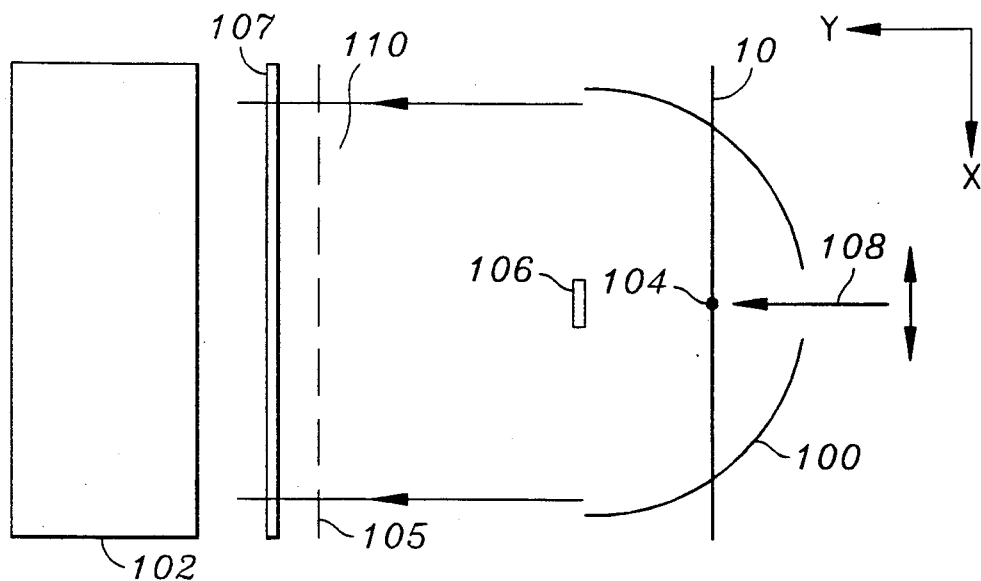
FIG. 10 is a schematic diagram of fluorescence collection and collimation using a paraboloid reflector.

FIG. 10 shows laser-induced fluorescence detection of capillary electrophoresis in which a paraboloid reflector 100 is utilized to efficiently collect and collimate the fluorescence emissions from a sample in a capillary 10 for detection by a photomultiplier tube 102. See copending U.S. patent application Ser. No. 07/772,823 filed Oct. 8, 1991 (Beckman) which is commonly assigned to the assignee of the present invention and is incorporated by reference herein. The capillary is positioned to pass through the focus 104 of the paraboloid. There is a strip 106 of material provided across the mouth of the paraboloid to block scatter from the capillary in the plane perpendicular to the capillary. In order for proper collimation of the fluorescence emission from the capillary detection section, the laser beam 108 should be directed at the focus of the paraboloid. Once the lateral alignment of the laser beam and the capillary column have been achieved as described above, alignment of the laser beam 108 with the capillary detection section at the focus of the paraboloid is determined by looking at the shadow of the blocking strip 106 at a plane 105 across the collimated light 110 in front of the filter 107.

Figure 11A:
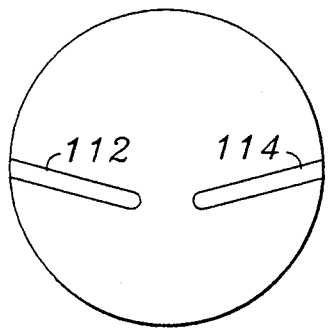
FIGS. 11A-C are images showing the shadow of the blocking strip at various positions of the laser beam with respect to the focus of the paraboloid reflector.
Figure 11B:
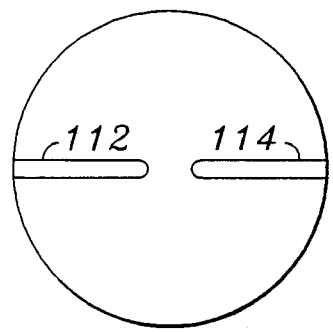
Figure 11C:
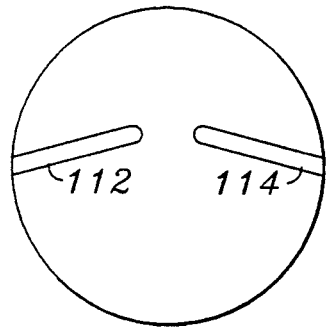

Referring to FIGS. 11A-C, when the laser beam is aligned with the focus of the paraboloid, the image of FIG. 11B is observed. The shadow of the blocking strip 106 appears as two disjointed dark sections 112 and 114 with the background of the scattered light. The reason for the disjointment in the shadow is not understood. If the laser beam is translated upwards in the X-direction from this aligned position, the dark sections 112 and 114 will bow downwards as shown in FIG. 11A. If the laser beam is translated in the opposite direction from the aligned position, the dark sections 112 and 114 will bow upwards as shown in FIG. 11C. Accordingly, by observing the image in the collimated beam, one can determined that the laser beam is aligned with the detection section of the capillary at the focus of the paraboloid. One can also determine the FIG. 11B alignment position by checking the photomultiplier signal (with the image plane 105 removed) which will be a minimum when the FIG. 11B image is achieved.

It is understood that the alignment of the laser beam with the focus of the paraboloid can be performed first and then the lateral alignment of the laser beam with the capillary column.

While the invention has been described with respect to the illustrated embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

I claim:

1. An apparatus for aligning a capillary with respect to a radiation source comprising:
   a capillary tube defining a capillary channel;
   radiation means for illuminating a defined section of the capillary channel, the illumination from the radiation means optically interacting with the capillary tube to produce a distinct light pattern; and
   alignment means for aligning the capillary channel with respect to the radiation means based on the distinct light pattern.

2. An apparatus as in claim 1 wherein the alignment means comprises detection means for detecting the distinct light pattern.

3. An apparatus as in claim 2 wherein the alignment means further comprises control means for controlling alignment of the capillary channel with respect to the radiation means based on feedback from the detected light pattern.

4. An apparatus as in claim 3 wherein the illumination from the radiation means interacts with the capillary tube to produce a light pattern from light scattering at inner wall of the capillary tube, and the detection means comprises at least a sensor positioned in an image plane outside of the capillary tube for detecting said scattered light pattern.

5. An apparatus as in claim 4 wherein there are at least two sensors positioned in the image plane for detecting intensities of scattered light from two points on the inner wall of the capillary channel in its diametral plane and providing feedback to the control means for alignment.

6. An apparatus as in claim 5 wherein the detection means further comprises means for imaging the diametral plane of the capillary channel onto the image plane.

7. An apparatus as in claim 6 wherein the image plane is defined by a plate having an aperture defined thereon wherein the aperture is sized to allow passage of fluorescent light but small enough to block scattered light from the capillary channel.

8. An apparatus as in claim 7 wherein the sensors are positioned near the aperture.

9. An apparatus as in claim 8 wherein the radiation means also causes fluorescence of contents in the capillary channel.

10. An apparatus as in claim 9 wherein the radiation means comprises a laser.

11. An apparatus as in claim 1 wherein the illumination from the radiation means interacts with the capillary tube to produce a pattern of an elongated spot having an intensity distribution of transmitted illumination from the radiation means onto the image plane, whereby the capillary channel is aligned with respect to the radiation means based on the intensity distribution of the spot.

12. An electrophoresis apparatus comprising:
    a capillary tube defining a separation channel;
    means for causing electrophoresis of a sample to separate into its components;
    radiation means for illuminating a defined section of the capillary channel, the illumination from the radiation means optically interacting with the capillary tube to produce a distinct light pattern; and alignment means for aligning the capillary channel with respect to the radiation means based on the distinct light pattern.

13. A method of aligning a capillary with respect to a radiation source comprising the steps of:
providing a capillary tube which defines a capillary channel;
providing a radiation means for illuminating a defined section of the capillary channel, the illumination optically interacting with the capillary tube to produce a distinct light pattern; and
aligning the capillary channel with respect to the radiation means based on the distinct light pattern.

14. A method as in claim 13 wherein the aligning step comprises detecting the distinct light pattern.

15. An apparatus as in claim 14 wherein the aligning step further comprises controlling alignment of the capillary channel with respect to the radiation means based on feedback from the detected distinct light pattern.

16. A method as in claim 15 wherein the illumination from the radiation means interacts with the capillary tube to produce a light pattern from light scattering at inner wall of the capillary tube and the detecting step further comprises providing at least a sensor positioned in an image plane outside of the capillary tube for detecting scattered light.

17. A method as in claim 16 wherein alignment of the capillary channel with respect to the radiation means is deemed achieved when scattered light from two points on the inner wall of the capillary channel in its diametral plane are of intensities that are substantially equal or in a given ratio, and wherein there are at least two sensors positioned in the image plane for detecting said scattered light from said two points and providing feedback to the control means.

18. A method as in claim 17 wherein the detecting step further comprising imaging the diametral plane of the capillary channel onto the image plane.

19. A method as in claim 18 wherein the detecting step comprises providing a plate having an aperture which defines the image plane wherein the aperture is sized to block scattered light from the capillary channel.

20. A method as in claim 19 wherein the sensors are positioned near the aperture.

21. A method as in claim 20 wherein the radiation means also causes fluorescence of contents in the capillary channel.

22. A method as in claim 21 wherein the radiation means comprises a laser.

23. A method as in claim 13 wherein the illumination from the radiation means interacts with the capillary tube to produce a pattern of an elongated spot having an intensity distribution of transmitted illumination from the radiation means onto the image plane, whereby the capillary channel is deemed aligned with respect to the radiation means by observing the intensity distribution of the spot.

24. A method of electrophoresis comprising the steps of:
providing a capillary tube which defines a separation channel;
causing electrophoresis of a sample to separate into its components;
providing a radiation means for illuminating a defined section of the separation channel, the illumination from the radiation means optically interacts with the capillary to produce a distinct light pattern; and
aligning the separation channel with respect to the radiation means based on the distinct light pattern.

* * * * *